(12) United States Patent
Masuya et al.

(10) Patent No.: US 11,506,675 B2
(45) Date of Patent: Nov. 22, 2022

(54) INSPECTION DEVICE

(71) Applicant: HITACHI HIGH-TECH CORPORATION, Tokyo (JP)

(72) Inventors: Akira Masuya, Tokyo (JP); Hiroko Fujita, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 228 days.

(21) Appl. No.: 16/494,477

(22) PCT Filed: Mar. 28, 2017

(86) PCT No.: PCT/JP2017/012603
§ 371 (c)(1),
(2) Date: Sep. 16, 2019

(87) PCT Pub. No.: WO2018/179081
PCT Pub. Date: Oct. 4, 2018

(65) Prior Publication Data
US 2020/0018774 A1    Jan. 16, 2020

(51) Int. Cl.
| | | |
|---|---|---|
| G01N 35/00 | (2006.01) |
| G01K 13/00 | (2021.01) |
| G01N 21/27 | (2006.01) |
| G01N 21/51 | (2006.01) |
| G01N 35/02 | (2006.01) |

(52) U.S. Cl.
CPC ....... *G01N 35/00584* (2013.01); *G01K 13/00* (2013.01); *G01N 21/272* (2013.01);
(Continued)

(58) Field of Classification Search
CPC .............. B01L 7/52; B01L 2300/1822; B01L 2200/025; F25B 21/04; F25B 2321/0251;
(Continued)

(56) References Cited

U.S. PATENT DOCUMENTS 9,993,824 B2 *  6/2018  Menges ............. G01N 21/0303
2006/0210435 A1 *  9/2006  Alavie ............... G01N 35/0092
422/65
(Continued)

FOREIGN PATENT DOCUMENTS

GB    1315767 A    5/1973
JP    2006187206 A    7/2006
(Continued)

OTHER PUBLICATIONS

Search Report dated Oct. 20, 2020 in corresponding in European Application No. 17902997.0.
(Continued)

*Primary Examiner* — Shogo Sasaki
(74) *Attorney, Agent, or Firm* — Miles & Stockbridge, P.C.

(57) ABSTRACT

The purpose of the present invention is to embody an inspection device wherein dew condensation in a sample container, in particular, in the lid thereof can be prevented or quickly removed without giving heat shock to a sample in the sample container. For this purpose, provided is an inspection device comprising an isothermal part 110 which comprises a rack 111 and maintains a sample container 150 storing a sample in a temperature-controlled environment, said sample container 150 comprising a plate and a lid, a detection part 120 which comprises an optical device for observing and inspecting the sample stored in the sample container, and a transportation part 130 which transports the sample container from the isothermal part to the detection part and vice versa, wherein at least one of the isothermal part, detection part and transportation part is provided with a member by which the lid of the sample container is held in a state lifted from the plate.

14 Claims, 9 Drawing Sheets

(52) U.S. Cl.
CPC ......... *G01N 21/51* (2013.01); *G01N 35/0099* (2013.01); *G01N 35/026* (2013.01); *G01N 2035/00455* (2013.01); *G01N 2201/0231* (2013.01)

(58) Field of Classification Search
CPC .... F25B 2321/0212; G01N 2201/0231; G01N 21/272; G01N 21/13; G01N 21/51; G01N 35/0099; G01N 35/02; G01N 2035/00455; G01N 35/00584; C12M 41/36; C12M 23/12; C12M 23/38; G01K 13/00

See application file for complete search history.

(56) References Cited

U.S. PATENT DOCUMENTS

| | | | | |
|---|---|---|---|---|
| 2008/0031774 | A1* | 2/2008 | Magnant | G01N 35/00722 700/214 |
| 2011/0165628 | A1* | 7/2011 | Verhaar | B01L 3/50851 435/303.1 |
| 2012/0149020 | A1* | 6/2012 | Alvino | B01L 7/52 435/6.12 |
| 2014/0224507 | A1 | 8/2014 | Fripp et al. | |
| 2015/0224507 | A1* | 8/2015 | Menges | G01N 35/028 422/82.08 |

FOREIGN PATENT DOCUMENTS

| | | |
|---|---|---|
| JP | 2009296938 A | 12/2009 |
| JP | 2010158185 A | 7/2010 |
| JP | 201441121 A | 3/2014 |
| WO | 2016117185 A1 | 7/2016 |

OTHER PUBLICATIONS

International Search Report dated Jun. 13, 2017, for PCT/JP2017/012603.

* cited by examiner

[FIG. 1]
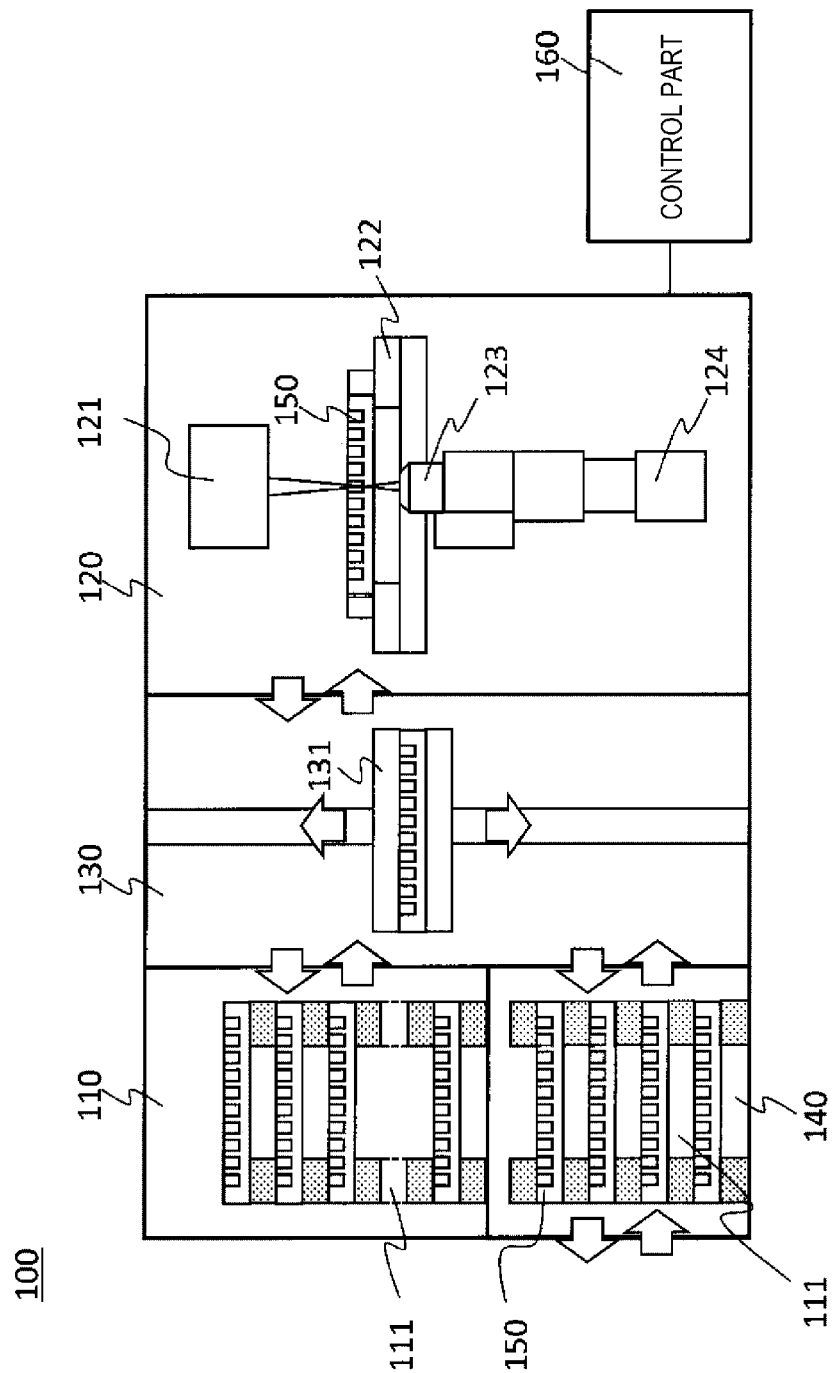

[FIG. 2A]
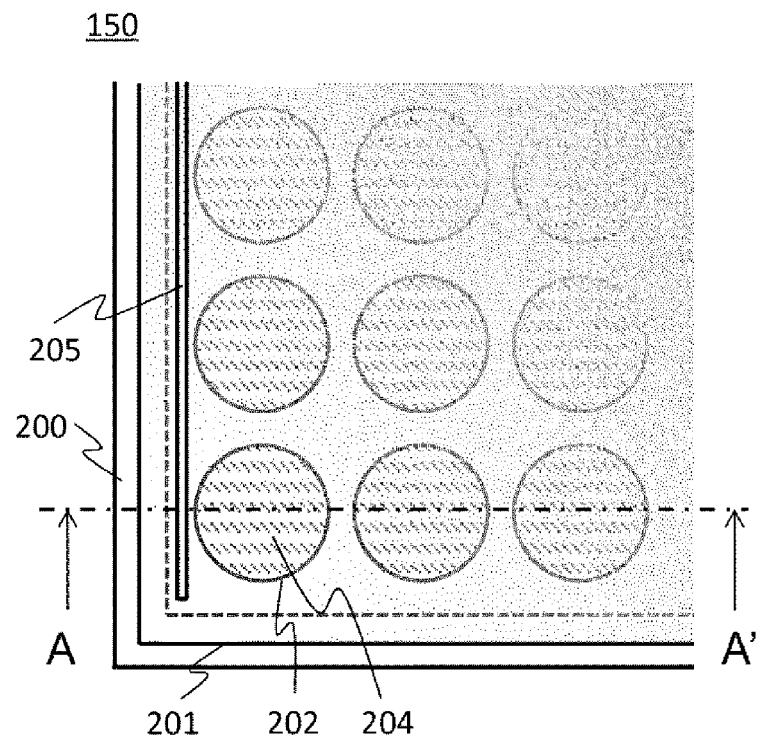
[FIG. 2B]
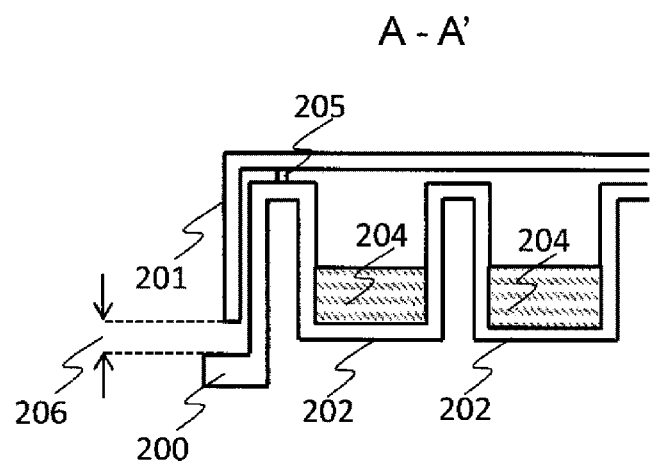

[FIG. 3A]
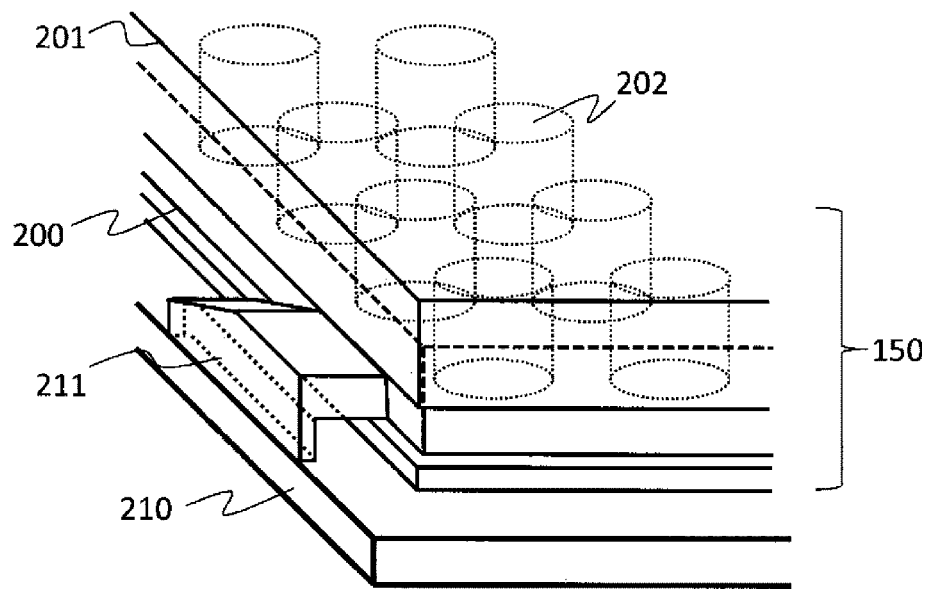
[FIG. 3B]
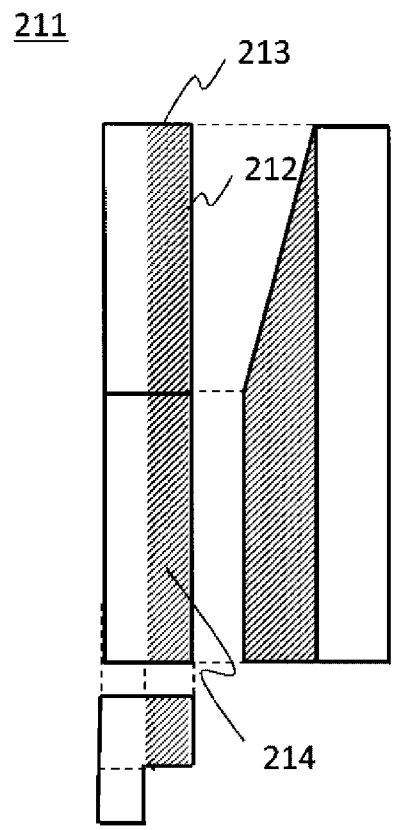

[FIG. 3C]
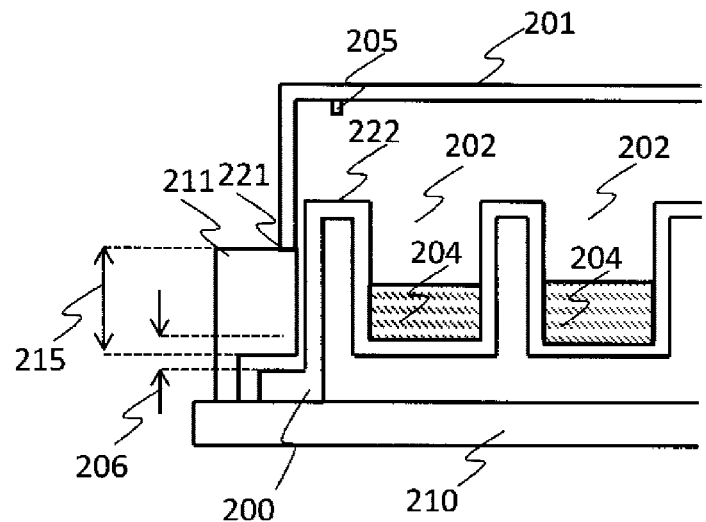
[FIG. 4A]
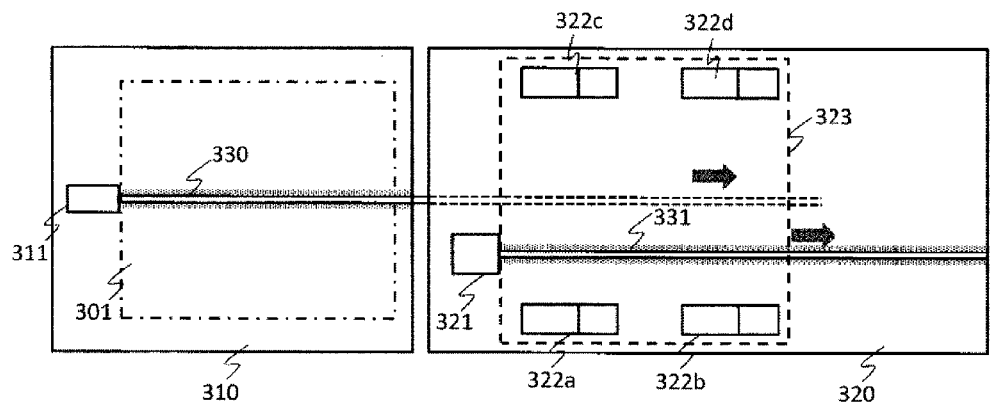
[FIG. 4B]
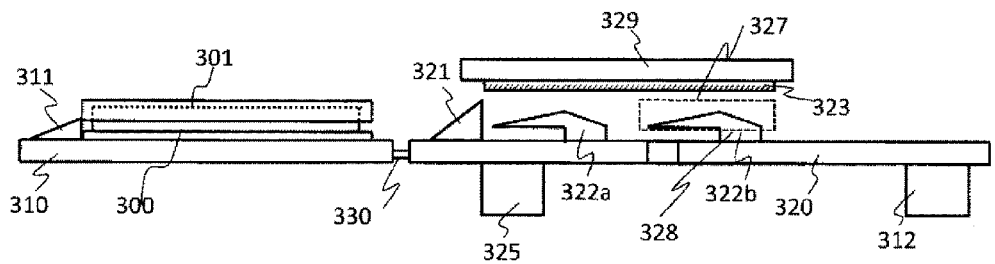

[FIG. 4C]
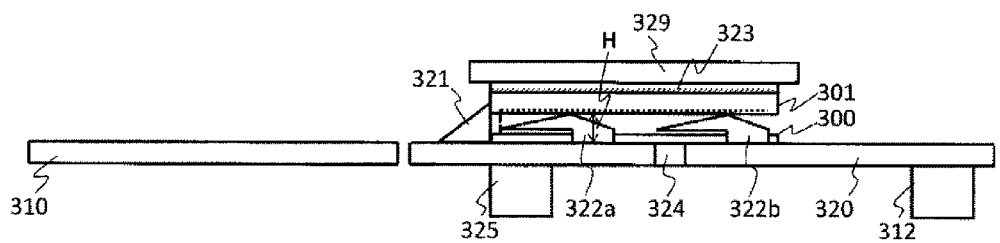
[FIG. 4D]
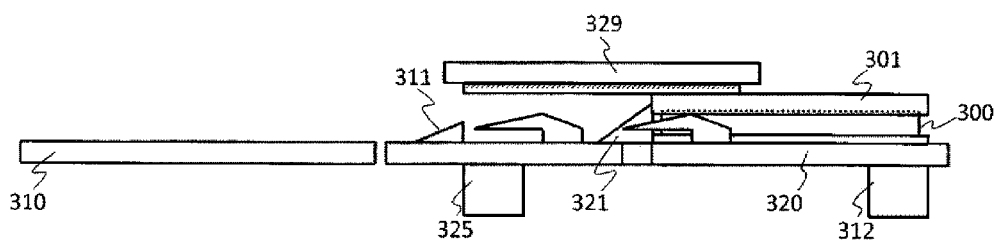
[FIG. 4E]
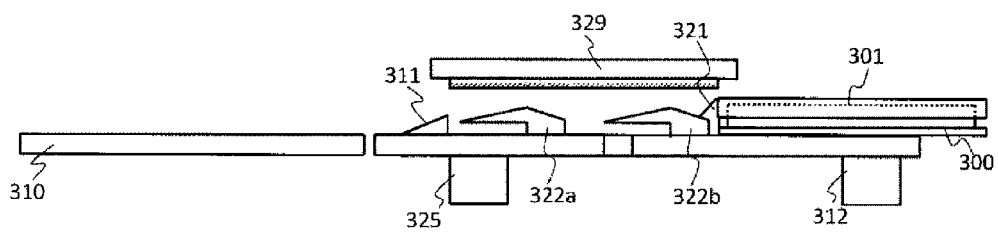
[FIG. 5A]
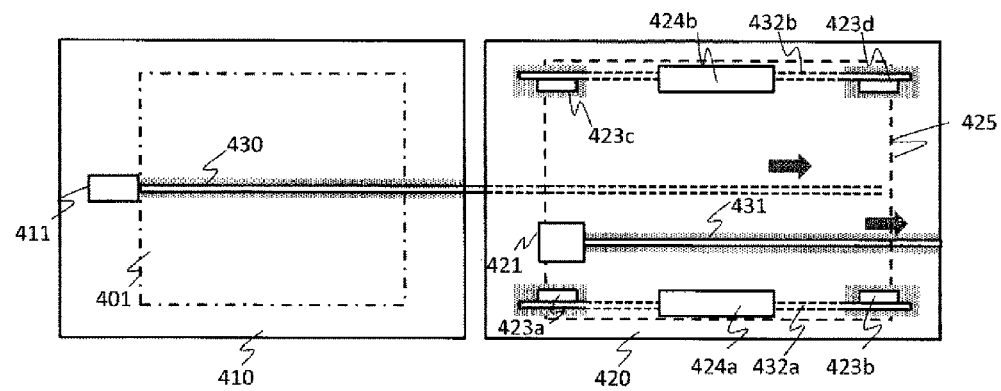

[FIG. 5B]
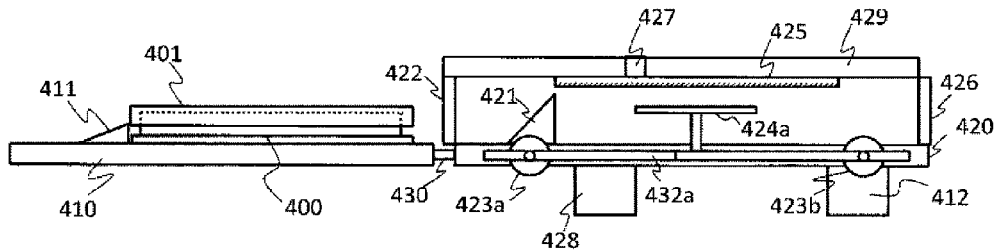
[FIG. 5C]
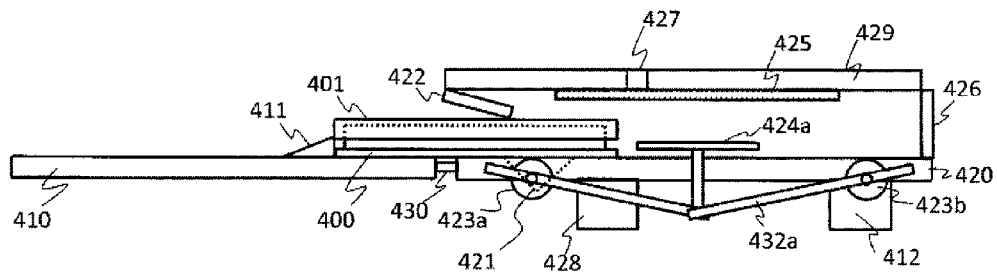
[FIG. 5D]
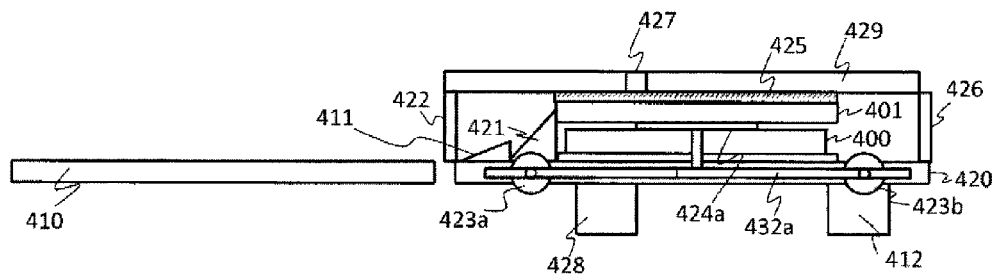
[FIG. 5E]
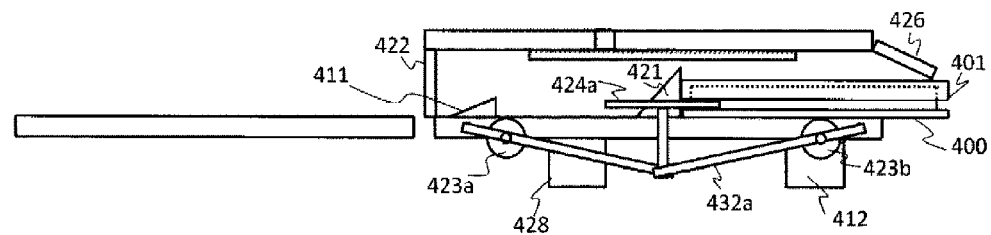

[FIG. 6A]
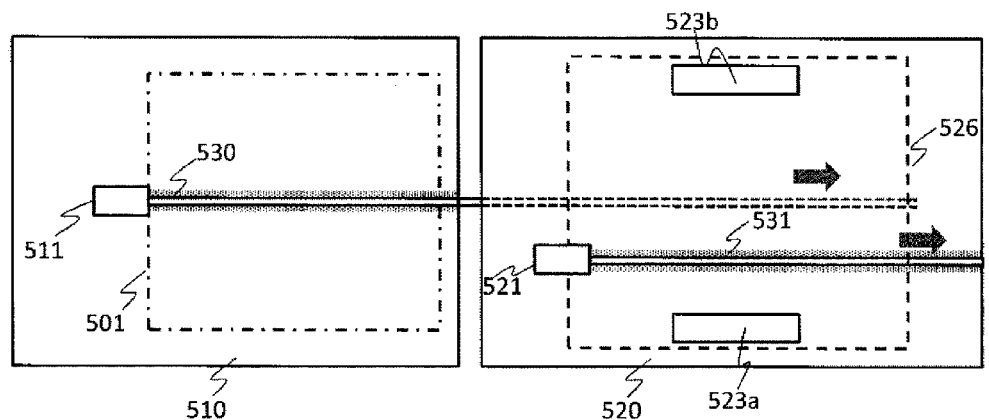
[FIG. 6B]
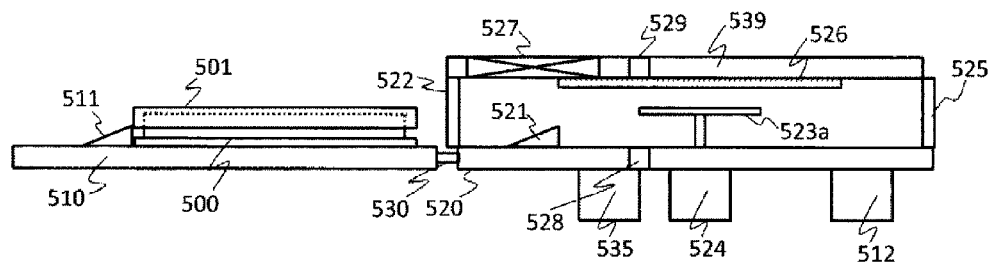
[FIG. 6C]
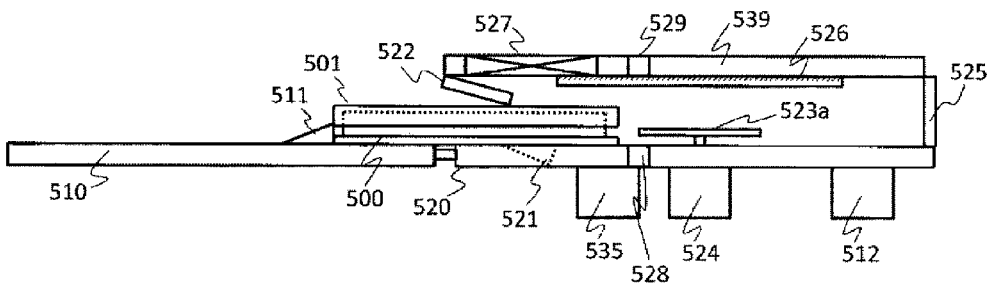

[FIG. 6D]
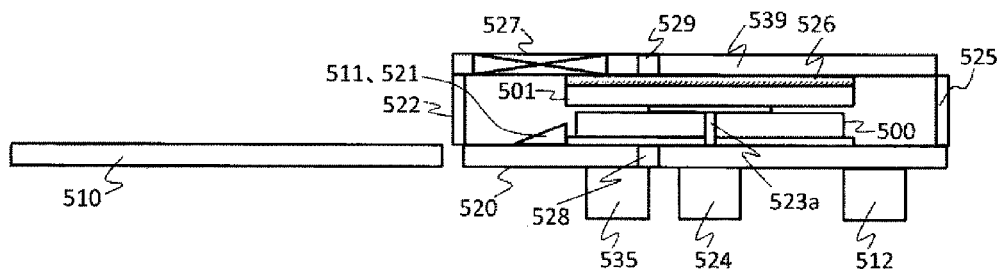
[FIG. 6E]
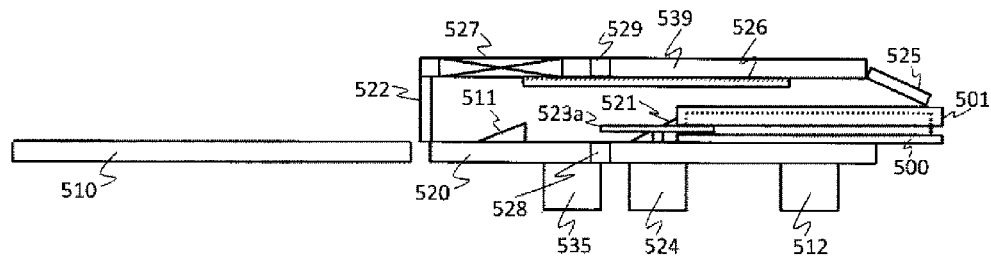
[FIG. 7A]
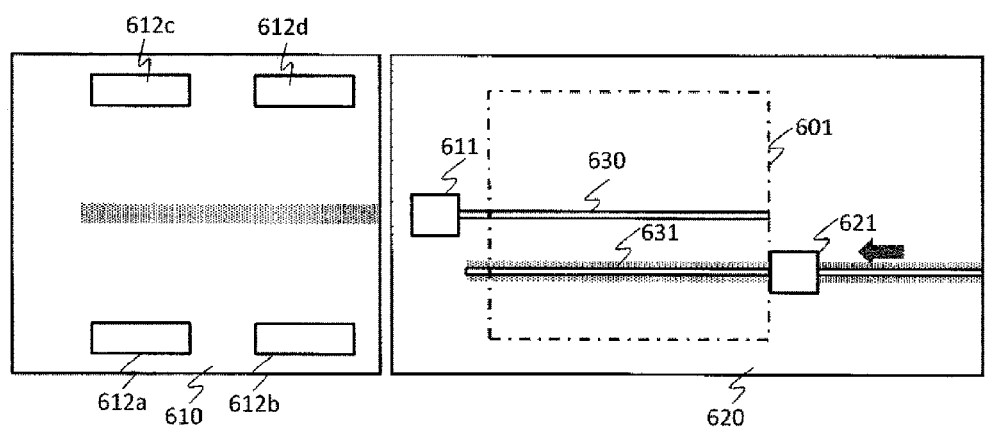

[FIG. 7B]
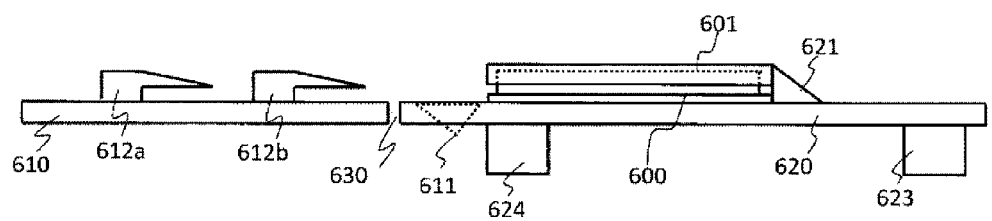
[FIG. 7C]
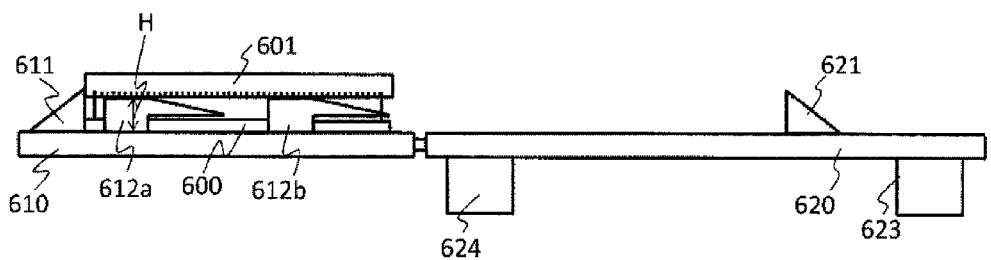

INSPECTION DEVICE

TECHNICAL FIELD

The present invention relates to an inspection device in which dew condensation in a sample container is prevented or removed and a sample in the sample container is observed and inspected.

BACKGROUND ART

In clinical institutions such as medical research institutions and hospitals, microscopy observation, particularly fluorescence microscopy observation for cell activity or the like is performed a plurality of times during cell culture, and an inspection is performed based on time-lapse observation for observing a dynamic change, and based on optical measurement results such as absorbance, fluorescence, and turbidity for bacteria identification and drug resistance. Since a specimen sample to be subjected to these observation and inspection is a biological sample, it is necessary to control a sample temperature by heating or the like. A culture temperature in a culture device needs to be controlled constant, but a temperature of a sample container temporally and spatially changes due to heat generated by a detector during sample observation and measurement after charging a sample into an inspection device, heat generated by an electric actuator that moves the sample container, and the like. Further, many biological samples are liquid samples and contain a lot of water. Therefore, water vapor is generated from the sample, and a moisture amount in air is large in the inspection device. The moisture amount in air is large and the temperature changes in the inspection device, so that in the inspection device, air in the sample container reaches a dew point that is a temperature at which dew condensation occurs, and it is often observed that the dew condensation occurs on an inner surface of the sample container, mainly on a lid.

In a case where dew condensation occurs on the inner surface of the sample container, when the sample is imaged through the sample container with a camera, shadows caused by the dew condensation overlap and the background of the image becomes not uniform. Accordingly, the contrast of the cell image is reduced, and the shape extraction performance of the cell is degraded. Light intensity of the background changes even when droplets of the dew condensation are small and the background is uniform, so that measures such as normalizing in image processing are required, which makes the image processing complicated. Similarly, the following problems occur in the optical measurement. When the absorbance measurement is performed, light scattering occurs due to minute droplets caused by the dew condensation that occurs on the lid, intensity of light emitted on the sample decreases while the light passes through the lid of the sample container, and thus an absorbance measurement value or a turbidity measurement value is changed. When the fluorescence measurement is performed, light scattering occurs due to minute droplets caused by the dew condensation that occurs on the lid, and thus intensity of excitation light by which photoexcitation is performed on the sample is changed while the excitation light passes through the lid of the sample container, and a measurement value of fluorescence intensity is changed. Generally, droplets of the dew condensation grow in size as time elapses, which also affects a condition of a surface where the dew condensation occurs, so that it is difficult to estimate an amount of light attenuation caused by the light scattering due to the dew condensation.

Thus, a device has been proposed which has a function of preventing dew condensation and a function of removing dew or haze generated in a culture container. In PTL 1, a culture container is set to a dew point temperature to an in-device temperature by providing a heater close to the culture container from at least one of an upper surface and a lower surface of the culture container and performing heating. PTL 2 provides an observation device. The observation device includes a mechanism in an imaging part and configured to perform heating, so that a surface temperature of a lid of a culture container is equal to a culture temperature of a sample. Dew condensation, which occurs when the culture container is relocated from a place where an environment such as a temperature is different, is removed by using a transparent heater or a fan that blows hot air.

PRIOR ART LITERATURE

Patent Literature

PTL 1: JP-A-2010-158185
PTL 2: JP-A-2009-296938

SUMMARY OF INVENTION

Technical Problem

Both PTL 1 and PTL 2 have limitations on a temperature at which the culture container can be heated to remove the dew condensation. This is because a heat shock may be applied to the sample in the culture container when heat is applied to the culture container at a temperature equal to or higher than the in-device temperature. PTL 1 discloses that when heating is performed from the upper surface of the culture container, heating to a temperature equal to or higher than the in-device temperature is also permitted, but it is inevitable that heat is transferred to the cells due to radiation or the like from the heater, and it is considered that substantial heating is practically difficult. For example, it is defined by the Clinical and Laboratory Standards Institute (CLSI) to maintain a temperature of a sample at 35° C.±2° C. in a bacterial inspection. Therefore, even when the culture container is heated because of dew condensation, the sample is not allowed to be heated at a temperature equal to or higher than that permitted.

On the other hand, particularly when the time-lapse observation is performed on bacteria, since growth of bacteria is generally rapid, it is necessary to shorten an observation period. In order to increase throughput of the inspection device, it is necessary to rapidly remove dew condensation before observation and inspection. Increasing a heating temperature is one method for removing the dew condensation, but when heat is applied at a temperature equal to or higher than the in-device temperature, the heat shock may be applied to the sample in the sample container as described above. On the other hand, the dew condensation cannot be removed in a short time by only heating to the in-device temperature.

Accordingly, in the inspection device in which the observation and the inspection of the sample is performed, it is required to prevent, or rapidly remove the dew condensation on the sample container, particularly on the lid, without giving a heat shock to the sample in the sample container.

Solution to Problem

Provided is an inspection device. The inspection device includes: an isothermal part that includes a rack and is configured to hold a sample container storing a sample in a temperature-controlled environment, the sample container including a plate and a lid; a detection part that includes an optical device configured to observe and inspect the sample stored in the sample container; and a transportation part that is configured to transport the sample container between the isothermal part and the detection part, in which a member configured to hold the lid of the sample container in a state of being lifted from the plate is provided in at least one of the isothermal part, the detection part, and the transportation part.

Advantageous Effect

It is possible to prevent or rapidly remove dew condensation on a sample container, particularly on a lid, without giving a heat shock to a sample in the sample container.

BRIEF DESCRIPTION OF DRAWINGS

FIG. 1 is a schematic view showing an overall structure of an inspection device.

FIG. 2A is a top view of a sample container.

FIG. 2B is a sectional view of the sample container.

FIG. 3A is a schematic explanatory view of a dew condensation prevention and removal mechanism.

FIG. 3B is a view illustrating a shape of a protrusion of the dew condensation prevention and removal mechanism.

FIG. 3C is a schematic explanatory view of the dew condensation prevention and removal mechanism.

FIG. 4A is a view illustrating the dew condensation removal mechanism and operation thereof.

FIG. 4B is a view illustrating the dew condensation removal mechanism and operation thereof.

FIG. 4C is a view illustrating the dew condensation removal mechanism and operation thereof.

FIG. 4D is a view illustrating the dew condensation removal mechanism and operation thereof.

FIG. 4E is a view illustrating the dew condensation removal mechanism and operation thereof.

FIG. 5A is a view illustrating a first modification of the dew condensation removal mechanism and operation thereof.

FIG. 5B is a view illustrating the first modification of the dew condensation removal mechanism and operation thereof.

FIG. 5C is a view illustrating the first modification of the dew condensation removal mechanism and operation thereof.

FIG. 5D is a view illustrating the first modification of the dew condensation removal mechanism and operation thereof.

FIG. 5E is a view illustrating the first modification of the dew condensation removal mechanism and operation thereof.

FIG. 6A is a view illustrating a second modification of the dew condensation removal mechanism and operation thereof.

FIG. 6B is a view illustrating the second modification of the dew condensation removal mechanism and operation thereof.

FIG. 6C is a view illustrating the second modification of the dew condensation removal mechanism and operation thereof.

FIG. 6D is a view illustrating the second modification of the dew condensation removal mechanism and operation thereof.

FIG. 6E is a view illustrating the second modification of the dew condensation removal mechanism and operation thereof.

FIG. 7A is a view illustrating the dew condensation prevention mechanism and operation thereof.

FIG. 7B is a view illustrating the dew condensation prevention mechanism and operation thereof.

FIG. 7C is a view illustrating the dew condensation prevention mechanism and operation thereof.

DESCRIPTION OF EMBODIMENTS

Hereinafter, preferred embodiments of the invention will be described with reference to the accompanying drawings. The embodiments described below show examples of typical embodiments of the invention, and the scope of the invention is not narrowly interpreted by the embodiments.

1. System Configuration of Inspection Device

FIG. 1 is a schematic view showing an overall system configuration and features of an inspection device 100. The inspection device 100 includes: an isothermal part 110 that holds sample containers 150 in an environment in which a temperature, humidity, carbon dioxide concentration, and the like are controlled; a detection part 120 that performs optical measurement on samples in the sample containers 150; a transportation part 130 that delivers the sample containers 150 between the isothermal part 110 and the detection part 120; and a sample charging part 140 that initially charges the sample containers 150 into the inspection device 100. The sample container 150 is not particularly limited, and it is desirable to use a 96-well plate or the like that can store a plurality of samples. The sample to be measured is not particularly limited, and may be a chemical reagent in addition to a biological sample such as a cell suspension or a bacterial suspension.

The isothermal part 110 includes racks 111 that can house the sample containers 150, and includes a heater (not shown) that adjusts a temperature of the isothermal part in order to perform reaction and culture by heating, a fan (not shown) that performs air convection, a humidity adjustment unit (not shown), a carbon dioxide gas exchange unit (not shown), and the like. The detection part 120 is provided with an optical device for observing and inspecting cells cultured in the sample container 150 in the example of FIG. 1, and includes a light source 121, a stage 122 that fixes the sample containers 150 during observation, a lens 123, and a detector 124. The stage 122 is preferably an electric stage, so that a measurement point can be moved to a plurality of sample storing portions of the sample containers 150. The stage 122 includes a sample container holding part that fixes the sample containers 150, and the sample container holding part includes, for example, a U-shaped sidewall and a bottom surface that is partially open for passing light from the light source 121 to a detector 124 side after transmitting the light through the sample containers 150. When an image inspection is performed, a camera unit such as a CCD is used in the detector 124. The transportation part 130 moves the sample containers 150 among the sample charging part 140, the isothermal part 110, and the detection part 120. The transportation part 130 includes a transportation mechanism 131 that pulls out or pushes the sample containers 150 which are disposed on the isothermal part 110, the detection part 120, or the sample charging part 140.

The isothermal part 110, the detection part 120 and the transportation part 130 that constitute the inspection device 100 include temperature adjustment mechanisms such as heaters to make a temperature environment controlled. On the other hand, the sample charging part 140 is set as an environment in which no reaction or culture is actively started. Thus, a dew condensation prevention and removal mechanism is provided in at least one of the isothermal part 110, the detection part 120, and the transportation part 130. Operation of the inspection device 100 is controlled by a control part 160.

2. Outline of Dew Condensation Prevention and Removal Mechanism

First, a top view of (a part of) the sample container 150 is shown in FIG. 2A, and a sectional view taken along A-A' of FIG. 2A is shown in FIG. 2B. The sample container 150 is a general sample container with a lid, and includes a plate 200 and a lid 201. The plate 200 includes a plurality of wells 202 that store samples 204. Further, the lid 201 is provided with a protruding portion 205 to reduce a contact point between the lid 201 and the plate 200. FIG. 2B shows a state where the lid 201 of the sample container 150 is closed, but in the state, there is a gap 206 between an upper surface of a bottom portion of the plate 200 and a lower surface of a side wall of the lid 201.

The dew condensation prevention and removal mechanism includes a member that holds the lid of the sample container 150 in a state of being lifted from the plate. FIGS. 3A, 3B, and 3C show an example of the member of the dew condensation prevention and removal mechanism. FIG. 3A shows a state where the lid of the sample container is lifted by the dew condensation prevention and removal mechanism. In the example shown in the figure, a protrusion 211 is provided on a pedestal 210 on which the sample container 150 is placed, and the lid 201 can be automatically raised and lowered as the sample container 150 is moved.

FIG. 3B shows three views of a shape of the protrusion 211. The protrusion 211 includes a lift portion configured to hold the lifted lid of the sample container and a column configured to support the lift portions. In the example of FIG. 3B, hatched portions represents the lift portion, and other portions represents the column. In this example, the protrusion 211 is fixed to the pedestal 210 by the column. The lift portion of the protrusion 211 is provided with an inclined surface 212 having a predetermined inclination with respect to the pedestal 210. First, an end portion 213 of the inclined surface enters the gap 206 (see FIG. 2B) between the plate 200 and the lid 201. While the sample container 150 is pulled in by sliding along the pedestal 210, the lid 201 is lifted along the inclined surface 212 of the lift portion of the protrusion 211, so that the lid 201 of the sample container 150 is held in a state of being lifted from the plate 200. FIG. 3C is a sectional view taken along A-A' of FIG. 2A in a lid-lifted state. The lid 201 is lifted by the protrusion 211 by a height 215.

The lid 201 is lifted vertically with respect to a disposition surface of the sample container 150 and is kept in a state of being separated from the plate 200. However, at this time it is not desirable that the lid 201 and the plate 200 are completely separated from each other from a viewpoint of preventing contamination to the samples. That is, it is desirable that a lower end 221 of the side wall of the lid 201 in contact with an upper flat surface of the protrusion 211 is held in a state of being lower than an upper surface 222 of the plate 200. The shape of the protrusion 211 is not limited to that shown in the figure as long as there is an inclined surface along which the lid is lifted. For example, an upper flat surface 214 of the protrusion 211 acts to stably hold the lid, but the protrusion 211 may have a shape without the upper flat surface as long as the lid can be stably maintained by providing a plurality of protrusions. Further, the inclined surface is not limited to a flat surface, and a curved surface or an inclined surface formed of a plurality of flat surfaces having different inclined angles may be used.

When an image inspection for the sample (cells or the like) is performed, the sample container is moved in the inspection device as follows. In the following example, the dew condensation removal mechanism is provided in the transportation mechanism 131.

(1) The sample container 150 is disposed in the sample charging part 140. The sample container 150 is a general sample container with the lid as shown in FIG. 2A.

(2) The transportation part 130 pulls out the sample container 150 from the sample charging part 140, and the sample container 150 is held by the transportation mechanism 131 of the transportation part 130. When the sample container 150 is pulled from the sample charging part 140 into the dew condensation removal mechanism provided in the transportation mechanism 131, a distance between the plate and the lid is widened, and dew condensation that adheres to the lid is removed.

(3) The sample container 150 from which the dew condensation is removed is pushed onto the stage 122 of the detection part 120 by the transportation mechanism 131. The stage 122 aligns the sample container 150 to a position (well) where optical measurement of the sample container is performed. The sample in the sample container 150 is irradiated with the light from the light source 121. The lens 123 forms an image of the sample on the detector 124. Accordingly, an image of cells in an initial state where no culture is started is acquired.

(4) After acquiring the image of the cells, the sample container 150 is pulled out from the detection part 120 by the transportation mechanism 131. The sample container 150 is pushed into the isothermal part 110 held in an environment in which the culture is started, and the culture of the sample is started.

When other sample containers 150 are in the sample charging part 140, the processing (2) to (4) is performed for each of the sample containers 150.

(5) The cells in the sample container 150 are cultured in the isothermal part 110. The sample container is pulled out by the transportation part 130 according to a measurement schedule from the start of the culture. When the sample container 150 is pulled into the dew condensation removal mechanism provided in the transportation mechanism 131, the distance between the plate and the lid is widened, and the dew condensation that adheres to the lid is removed.

(6) The sample container 150 from which the dew condensation is removed is pushed onto the stage 122 of the detection part 120 by the transportation mechanism 131, and an image of the cells is acquired in the same manner as in (3). Accordingly, the image of the cells for which predetermined time has passed since the start of the culture is acquired.

(7) The processing of (4) to (6) is repeated, so that a temporal change in a state of the sample can be observed.

The above sequence is controlled by the control part 160. Image data, which is acquired observation data, is input to a personal computer or the like, and an inspection result of the cells is output based on the temporal change of the image.

Hereinafter, a configuration in which the dew condensation removal mechanism is provided in the transportation mechanism 131 will be described as a first embodiment. When the dew condensation removal mechanism is provided in the transportation mechanism 131, since dew condensation removal can be performed on the sample container to be subjected to the next observation and inspection while the sample is observed and inspected in the inspection part, the dew condensation removal can be performed without affecting the throughput of the inspection device. The dew condensation removal mechanism may also be provided in the detection part 120, and in this case, the dew condensation removal mechanism may be provided on the stage 122 of the optical device.

First Embodiment

The dew condensation removal mechanism of the first embodiment and operation thereof will be described with reference to FIGS. 4A to 4E. FIG. 4A shows a top view of a pedestal (here, simply referred to as a "rack") 310 of the rack of the isothermal part and a top view of a pedestal (here, simply referred to as a "pedestal") 320 of the transportation mechanism in which the dew condensation removal mechanism is provided, and FIG. 4B shows a side sectional view in the same state as FIG. 4A. That is, the sample container is placed on the rack 310 and is in a state before being pulled from the isothermal part into the transportation part. The pedestal 320 is provided with protrusions 322, which are partially different in shape from that in FIGS. 3A to 3C, and the protrusion 322 includes a lift portion 327 that is surrounded by a dotted line and a column 328 that supports the lift portion 327. A characteristic shape of the protrusion 322 in this example is that inclined surfaces are provided on both a left side and a right side of the lift portion 327. This is because, in the transportation mechanism, the sample container is transferred between the isothermal part (or the sample charging part) and the detection part. An arm a 311 is for pulling the sample container (indicated by a one-dot chain line in FIG. 4A) placed on the rack 310 onto the pedestal 320, and is driven by a motor a 312 provided below the pedestal 320 via a bar 330. Accordingly, the sample container (a plate 300 and a lid 301) is pulled onto the pedestal 320. An arm b 321 is for moving the sample container on the pedestal 320, but obstructs the movement of the sample container, at this time. Therefore, when the sample container is pulled onto the pedestal 320, it is desirable that the arm b 321 sinks into the pedestal 320, and after the sample container passes an upper portion of the arm b 321, the arm b 321 protrudes from a horizontal surface of the pedestal 320 by a spring or the like and returns to an initial state. After the sample container is moved to the pedestal 320, the arm a 311 returns to a position of an initial state again by the motor a 312.

FIG. 4C shows a state after the sample container is pulled from the rack 310 into the transportation mechanism. The dew condensation removal mechanism includes protrusions 322a to 322d and a heater 323 (indicated by a dotted line in FIG. 4A) that is provided on a top plate 329, lifts the lid of the sample container pulled into the dew condensation removal mechanism by the arm a 311, and heats the lid in the lid-lifted state by the heater 323, so as to remove the dew condensation. Since the lid is heated in the lid-lifted state, a temperature of the heater 323 can be set higher than a set temperature of the isothermal part. As described above, the lift portions of the protrusions 322a to 322d have the inclined surfaces on both the side where the sample container is pulled in and the side where the sample container is discharged. However, the lift portions of the protrusions 322a and 322c may have shapes in which no inclined surface is provided on the side where the sample container is discharged, and the lift portions of the protrusions 322b and 322d may have shapes in which no inclined surface is provided on the side where the sample container is pulled in. As shown in FIG. 4C, when the sample container is transferred from the rack 310 of the isothermal part to the pedestal 320 of the transportation mechanism, the lid 301 is lifted upwardly from the plate 300 by the protrusions 322 fixed to the pedestal 320, and is adjusted such that a distance between the plate 300 and the lid 302 is increased. A height H of the protrusions 322 is set to be lower than a height of the plate 300. Accordingly, as described above, in the state where the lid 301 is lifted, a lower end of a side wall of the lid 301 in contact with upper portions of the protrusions 322 is held in a state of being lower than an upper surface of the plate 300.

The heater 323 heats an upper surface of the lid 301 that is lifted by the protrusions 322. As the heater 323, a sheet-shaped heater, for example, a glass heater, a rubber heater, a carbon heater, or the like can be used. The heat output from the heater 323 to the lid 301 can also be controlled by adjusting a distance between the heater 323 and the lid 301. A temperature detector 324, which monitors a temperature on a bottom surface of the plate 300 that is provided on the pedestal 320 of the transportation mechanism, monitors whether a temperature of the samples in the plate 300 is excessively raised due to the heating of the heater 323. The output and heating time of the heater 323 may be adjusted based on a measured temperature of the temperature detector 324. For example, when a set temperature of the heater 323 is about 50° C. and the lid 301 close to the heater by being suspended from the plate is heated about 1 minute, the dew condensation can be removed. Further, when the temperature of the samples monitored by the temperature detector is higher than a predetermined temperature, the heating by the heater can be controlled to be stopped.

FIG. 4D shows a process in which the sample container passes the pedestal 320. After the dew condensation is removed, the sample container is pulled out from the dew condensation removal mechanism by the arm b 321. The arm b 321 is driven by a motor b 325 provided below the pedestal 320 via a bar 331 (see FIG. 4A). Accordingly, the sample container is moved to the detection part. The arm b 321 has a sufficient height to simultaneously move the lid 301 in the lid-lifted state and the plate 300.

FIG. 4E shows a state after the sample container is pulled out from the dew condensation removal mechanism, the distance between the plate 300 and the lid 301 is reduced, and an initial state is returned. After the sample container passes the dew condensation removal mechanism by the arm b 321, the lid 301 loses the support from the protrusions 322, so the distance between the plate 300 and the lid 301 is reduced, and an initial state is returned. The arm b 321 continues to be driven by the motor b 325, and the sample container is transported to the detection part.

In this way, by heating the lid with a distance kept between the plate and the lid, the temperature is raised at which the lid can be heated without generating a heat shock to the sample, surrounding air is taken into the sample container, and moisture-containing air in the sample container is discharged out of the sample container, so that the time required for removing the dew condensation can be shortened.

The shape of the protrusion 322 is not limited to the shown shape. For example, two protrusions are provided on the two side surfaces of the pedestal in the figure, but one protrusion may be provided on the two side surfaces of the pedestal with the lift portion being trapezoidal. Further, since the column of the protrusion 322 may be fixed such that the lift portion of the protrusion 322 is positioned in the gap between the lid and the plate of the sample container when the sample container is transferred, various modifications can be made. For example, the column may be provided on the top plate 329, or may be provided on a side wall (not shown) or a column (not shown) of the transportation mechanism 131 according to a shape of the transportation mechanism 131.

A first modification of the dew condensation removal mechanism will be described with reference to FIGS. 5A to 5E. The first modification is described also based on a configuration in which the dew condensation removal mechanism is provided in the transportation mechanism 131. In the configuration of FIGS. 4A to 4E, since the lid of the sample container is lifted by the inclined portions of the protrusions, a gradient of the inclined surfaces of the protrusions needs to be steep in order to increase the height to which the lid is lifted. Accordingly, the friction between the lid and the inclined surfaces of the protrusions increases, and thus the lid may not be smoothly lifted. On the other hand, by lifting the lid higher, it is unlikely to generate a heat shock to the samples even if the temperature of heating the lid is further increased, and it is easier to discharge the moisture-containing air out of the sample container, so that an effect of removing the dew condensation can be enhanced. The first modification relates to the dew condensation removal mechanism capable of lifting the lid of the sample container higher with a simple structure.

FIG. 5A shows a top view of a rack 410 of the isothermal part and a top view of a pedestal 420 of the transportation mechanism in which the dew condensation removal mechanism is provided, and FIG. 5B shows a side sectional view in the same state as FIG. 5A. The sample container is provided on the rack 410 of the isothermal part, and is in a state before being pulled from the isothermal part into the transportation part. An arm a 411 is for pulling the sample container (indicated by a one-dot chain line in FIG. 5A) placed on the rack 410 of the isothermal part onto the pedestal 420 of the transportation mechanism, and is driven by a motor a 412 provided below the pedestal 420 via a bar 430. Accordingly, the sample container (a plate 400 and a lid 401) is pulled onto the pedestal 420. In the transportation mechanism, side walls are provided on side surfaces as a front surface and a back surface in the figure, and a door a 422 and a door b 426 are movably attached to a top plate 429 on side surfaces as an inlet and an outlet of the sample container.

FIG. 5C shows a state where the sample container is being pulled from the rack 410 into the transportation part. An arm b 421 is for moving the sample container onto the pedestal 420, but obstructs the movement of the sample container at this time. Therefore, when the sample container is pulled onto the pedestal 420, it is desirable that the arm b 421 sinks into the pedestal 420, and after the sample container passes an upper portion of the arm b 421, the arm b 421 protrudes from a horizontal surface of the pedestal 420 by a spring or the like, and returns to an initial state. After the sample container is moved to the pedestal 420, the arm a 411 returns to a position of an initial state again by the motor a 412. The dew condensation removal mechanism includes protrusions 424a and 424b and a heater 425 (indicated by a dotted line in FIG. 5A) that is provided on the top plate 429, lifts the lid of the sample container pulled into the dew condensation removal mechanism by the arm a 411, and heats the lid by the heater 425 in the lid-lifted state, so as to remove the dew condensation. Here, the protrusions 424 are vertically movable, and include rollers 423a to 423d and shafts 432a and 432b as mechanisms for vertically moving the protrusions 424. The protrusion 424 has a lift portion that holds the lid of the sample container and a column that connects the lift portion to the shaft.

As shown in FIG. 5C, the sample container is pushed, by the arm a 411, onto the pedestal 420 of the transportation mechanism by passing through the door a 422 while the door a 422 is opened. The door a 422 and the door b 426 are provided to limit the movement of air in a space around the sample container in the transportation part in order to reduce a risk of contamination during a period in which the lid 401 of the sample container is greatly lifted in the transportation part. When the sample container is pushed onto the pedestal 420 by the arm a 411, the rollers 423a and 423c are pushed down. The pushed-down roller 423 pushes down the protrusion 424 via the shaft 432, and a height of the lift portion of the protrusion 424 is set to allow the lift portion to enter a gap between the plate 400 and the lid 401. Further, it is desirable that a thickness of the lift portion is thin, so that the lift portion enters the gap between the plate 400 and the lid 401 easily. For example, when there is no action of force from the roller 423, the protrusion 424 returns to an initial state by, for example, a spring (not shown) or the like.

FIG. 5D shows a state where the sample container is completely transferred onto the pedestal 420. Since the sample container passes across the rollers 423a and 423c, as the roller 423 moves to return to an initial state, the protrusion 424 also returns to an initial state. When the protrusion 424 returns to an initial state, the lid 401 is lifted. Although not limited, it is desirable that a lower end of a side wall of the lid 401 in contact with the lift portion is held in a state of being higher than an upper surface of the plate 400. Accordingly, exchange of air in the sample container is easier. The heater 425 is disposed on the top plate 429, and the protrusion 424 is adjusted, for example, to a height at which the lid 401 is in contact with the heater 425. Alternatively, the heat output from the heater 425 to the lid 401 may be controlled by adjusting a distance between the heater 425 and the lid 401. In a state where the sample container is completely transferred onto the transportation part, the door a 422 and the door b 426 are closed, and a space around the sample container is blocked from a space of the transportation part. The movement of air in the space around the sample container is limited, so that it is effective to prevent occurrence of contamination particularly in a state where the lower end of the side wall of the lid 401 is held higher than the upper surface of the plate 400.

A dew condensation detector 427 provided on the top plate 429 monitors a dew condensation state on the lid 401. In this example, the lid can be heated without adversely affecting the samples by widely separating the lid 401 from the plate 400. Therefore, a degree of the dew condensation on the lid 401 can be detected by the dew condensation detector 427, and the output and heating time of the heater 425 can be adjusted. For example, the dew condensation detector 427 detects scattered light caused by the dew condensation that adheres to the lid 401, and determines the degree of the dew condensation. In this case, it is desirable that the heater 425 is a transparent glass heater. Alternatively, a rubber heater or a carbon heater may be used in which a transparent window is provided on a portion where the dew condensation detector 427 is provided. Further, a temperature detector may be provided to monitor a temperature of a bottom surface of the plate 400, which is similar to the examples of FIGS. 4A to 4E.

FIG. 5E shows a state where the sample container is being discharged from the transportation part by the arm b 421.

The arm b 421 is driven by a motor b 428. The sample container is discharged by pushing down the rollers 423b and 423d. The pushed-down roller 423 pushes down the protrusion 424 via the shaft 432, and the height of the lift portion of the protrusion 424 is set to allow the lift portion to enter the gap between the plate 400 and the lid 401. Accordingly, a distance between the plate 400 and the lid 401 returns to an initial state. The sample container passes through the door b 426 while the door b 426 is opened. The arm b 421 continues to be driven by the motor b 428, and the sample container is transported to the detection part.

A second modification of the dew condensation removal mechanism will be described with reference to FIGS. 6A to 6E. The second modification is described also based on a configuration in which the dew condensation removal mechanism is provided in the transportation mechanism 131. A member that adjusts a height to which the lid of the sample container is lifted in the dew condensation removal mechanism is the protrusion same as that of the first modification, but is an example that allows more flexible control. For example, the height to be lifted can be programmed according to the sample container.

FIG. 6A shows a top view of a rack 510 of the isothermal part and a top view of a pedestal 520 of the transportation mechanism in which the dew condensation removal mechanism is provided, and FIG. 6B shows a side sectional view in the same state as FIG. 6A. FIG. 6B shows the sample container is provided on the rack 510 and is in a state before being pulled from the isothermal part into the transportation part. An arm a 511 is for pulling the sample container (indicated by a one-dot chain line in FIG. 6A) placed on the rack 510 onto the pedestal 520, and is driven by a motor a 512 provided below the pedestal 520 via a bar 530. Accordingly, the sample container (a plate 500 and a lid 501) is pulled onto the pedestal 520. In the transportation mechanism, side walls are provided on side surfaces as a front surface and a back surface in the figure, and a door a 522 and a door b 526 are movably attached to a top plate 539 on side surfaces as an inlet and an outlet of the sample container.

FIG. 6C shows a state where the sample container is being pulled from the rack 510 of the isothermal part into the transportation part. An arm b 521 is for moving the sample container on the pedestal 520, but obstructs the movement the sample container at this time. Therefore, when the sample container is pulled onto the pedestal 520, it is desirable that the arm b 521 sinks into the pedestal 520, and after the sample container passes an upper portion of the arm b 521, the arm b 521 protrudes from a horizontal surface of the pedestal 520 by a spring or the like, and returns to an initial state. After the sample container is moved to the pedestal 520, the arm a 511 returns to a position of an initial state again by the motor a 512. The dew condensation removal mechanism includes protrusions 523a and 523b and a heater 526 (indicated by a dotted line in FIG. 6A) that is provided on the top plate 539, lifts the lid of the sample container pulled into the dew condensation removal mechanism by the arm a 511, and heats the lid in the lid-lifted state by the heater 526, so as to remove the dew condensation. Here, the protrusions 523 are vertically movable, and include actuators 524 as mechanisms for vertically moving the protrusions 523. The protrusion 523 includes a lift portion that is the same as that of the first modification and holds the lid of the sample container, and a column that connects the lift portion to the actuator 524.

As shown in FIG. 6C, the sample container is pushed, by the arm a 511, onto the pedestal 520 by passing through the door a 522 while the door a 522 is opened. The door a 522 and the door b 525 are provided to limit the movement of air in a space around the sample container in the transportation part so as not to generate contamination during a period in which the lid 501 of the sample container is greatly lifted in the transportation part. The actuator is controlled by the control part 160 (see FIG. 1), so that the lift portion of the protrusion 523 has a height that allows the lift portion to enter a gap between the plate 500 and the lid 501 when the sample container is pushed onto the pedestal 520 of the transportation mechanism by the arm a 511. Further, it is desirable that a thickness of the lift portion is thin, so that the lift portion enters the gap between the plate 500 and the lid 501 easily.

FIG. 6D shows a state where the sample container is completely transferred onto the pedestal 520. In this state, the actuator is controlled by the control part 160 (see FIG. 1) to lift the lid 501 by the protrusion 523. Although not limited, it is desirable that a lower end of a side wall of the lid 501 in contact with the lift portion is maintained higher than an upper surface of the plate 500. The heater 526 is disposed above the lid 501, and the protrusion 523 is adjusted, for example, to a height at which the lid 501 is in contact with the heater 526. Alternatively, the heat output from the heater 526 to the lid 501 may be controlled by adjusting a distance between the heater 526 and the lid 501. In a state where the sample container is completely transferred onto the transportation part, the door a 522 and the door b 525 are closed, and a space around the sample container is blocked from a space of the transportation part. Further, in the present modification, air may be circulated by a fan 527 between the space of the transportation part and the space blocked by the door a 522 and the door b 525. When outside air is to be taken in, air purified by an HEPA filter or the like is taken in, and at an air discharge port that discharges the taken-in air to outside, the air is also purified by the HEPA filter or the like and then is discharged to the outside. Accordingly, moisture-containing air is discharged from the space blocked by the door a 522 and the door b 525, and the sample container can be held in a relative lower humidity environment.

A temperature detector 528, which monitors a temperature on a bottom surface of the plate 500 disposed on the pedestal 520 of the transportation mechanism, monitors whether a temperature of the samples in the plate 500 is excessively raised due to the heating of the heater 526. The output and heating time of the heater 526 may be adjusted based on a measured temperature of the temperature detector 528. For example, when the temperature of the samples monitored by the temperature detector 528 is higher than a predetermined temperature, the heating by the heater 526 may be stopped, or the distance between the heater 526 and the lid 501 may be controlled to be increased. A dew condensation detector 529 provided on the top plate 539 monitors a dew condensation state on the lid 501. A degree of the dew condensation on the lid 501 may be detected by the dew condensation detector 529, and the output and the heating time of the heater 526 may be adjusted. For example, the dew condensation detector 529 detects scattered light caused by the dew condensation that adheres to the lid 501, and determines the degree of the dew condensation. In this case, it is desirable that the heater 526 is a transparent glass heater. Alternatively, a rubber heater or a carbon heater may be used in which a transparent window is provided in a portion where the dew condensation detector 529 is provided.

FIG. 6E shows a state where the sample container is being discharged from the transportation part by the arm b 521.

When air is circulated by the fan 527 between a surrounding space and the space blocked by the door a 522 and the door b 525, the operation of the fan 527 is stopped. The actuator is controlled by the control part 160 (see FIG. 1) to return a height of the protrusion 523 to a height of an initial state, and to return a distance between the plate 500 and the lid 501 an initial state. While the door b 525 is opened, the sample container passes through the door b 525 by the arm b 521 driven by a motor b 535. The arm b 521 continues to be driven by the motor b 535, and the sample container is transported to the detection part.

Thus, the first embodiment has been described in detail, including the modifications. These may be modified in various ways, and the constituent elements thereof may be applied to another example. For example, in the configuration shown in FIG. 4A, the doors or the fan may also be provided in the transportation mechanism. Further, when the dew condensation removal mechanism is provided on the stage of the optical device, the protrusion can be provided on the sample container holding part, the heater can be provided as a glass heater to be supported by a side wall of the sample container holding part, and the temperature detector can be provided on a bottom surface of the sample container holding part. The doors in the modifications may be provided on open surfaces of the side wall of the sample container holding part.

Second Embodiment

Hereinafter, a configuration in which the dew condensation prevention mechanism is provided on the rack of the isothermal part will be described in detail as a second embodiment. The temperature is controlled in a stable state in the isothermal part, but the sample container is placed in a high humidity state for a long period of time for sample culture, making the dew condensation easily occur even with a slight change in the temperature. Therefore, it is effective to provide a mechanism that reduces the dew condensation even in the isothermal part. The dew condensation prevention mechanism may be provided in the detection part or the transportation part, and in this case, may be separately provided on the stage of the optical device or in the transportation mechanism.

The dew condensation prevention mechanism of the second embodiment and operation thereof will be described with reference to FIGS. 7A to 7C. FIG. 7A shows a top view of a pedestal (here, simply referred to as a "rack") 610 of the rack of the isothermal part in which the dew condensation prevention mechanism is provided and a top view of a pedestal (here, simply referred to as "pedestal") 620 of the transportation mechanism, and FIG. 7B shows a side sectional view in the same state as FIG. 7A. The sample container is placed on the pedestal 620 and is in a state before being pushed from the transportation part into the isothermal part. An arm b 621 is for pushing the sample container (indicated by a one-dot chain line in FIG. 7A) placed on the pedestal 620 of the transportation mechanism onto the rack 610 of the isothermal part, and is driven by a motor b 624 provided below the pedestal 620 via a bar 631. Accordingly, the sample container (a plate 600 and a lid 601) is pushed onto the rack 610. An arm a 611 is for moving the sample container on the rack 610 to the pedestal 620, but obstructs the sample container at this time. Therefore, when the sample container is pushed onto the rack 610, it is desirable that the arm a 611 sinks into the pedestal 620, and after the sample container passes an upper portion of the arm a 611, the arm a 611 protrudes from a horizontal surface of the pedestal 620 by a spring or the like, and returns to an initial state.

FIG. 7C shows a state after the sample container is pushed onto the rack 610 of the isothermal part. The dew condensation prevention mechanism includes protrusions 612a to 612d, lifts the lid of the sample container, and allows humidity-containing air in the sample container to be dissipated to the surroundings, thereby preventing the dew condensation. As shown in FIG. 7C, when the sample container is transferred from the pedestal 620 of the transportation mechanism to the rack 610 of the isothermal part, the lid 601 is lifted upwardly from the plate 600 by the protrusion 612 fixed to the rack 610 and is adjusted to increase a distance between the plate 600 and the lid 601. A height H of the protrusion 612 is set to be lower than a height of the plate. Accordingly, in a state where the lid 601 is lifted, a lower end of a side wall of the lid 601 in contact with an upper portion of the protrusion 612 is maintained lower than an upper surface of the plate 600. The protrusion 612 is the same as the protrusion 322 described in the first embodiment. The protrusion 612 includes an upper surface parallel to the rack on a rack side of the isothermal part, and holds the lifted lid 601 stably. A shape of the protrusion 612 is not limited to that shown in the figures, and various modifications can be made as long as a column of the protrusion 612 can fix a corresponding lift portion at a predetermined height. For example, the column of the protrusion 612 may be provided on a back surface of the pedestal of the upper rack, or may be provided on a column that supports the rack.

When the sample container held on the rack 610 of the isothermal part is transferred into the transportation mechanism, the arm a 611 pulls the sample container onto the pedestal 620 of the transportation mechanism in the same manner as in the first embodiment. The arm a 611 is driven by a motor a 623 provided below the pedestal 620 via a bar 630.

The dew condensation prevention mechanism has been described above, but instead of the protrusion 612 fixed to the rack, a protrusion that is vertically movable can also be used as described in the first modification and the second modification of the first embodiment. Further, it is also possible to apply the first embodiment and the second embodiment in combination.

REFERENCE SIGN LIST 100 inspection device
110 isothermal part
111 rack
120 detection part
121 light source
122 stage
123 lens
124 detector
130 transportation part
131 transportation mechanism
140 sample charging part
150 sample container
160 control part
200, 300, 400, 500, 600 plate
201, 301, 401, 501, 601 lid
202 well
210, 320, 420, 520, 620 pedestal
211, 322, 424, 523, 612 protrusion
310, 410, 510, 610 rack
311, 411, 511, 611 arm a
312, 412, 512, 623 motor a
321, 421, 521, 530, 621 arm b
323, 425, 526 heater 324, 528 temperature detector
325, 428, 535, 624 motor b
329, 429, 539 top plate
422, 522 door a
423 roller
426, 525 door b
427, 529 dew condensation detector
524 actuator
527 fan

The invention claimed is:

1. An inspection device for inspecting a plurality of sample containers each having a plate and a lid and storing a sample, the inspection device comprising:
 a plurality of isothermal racks each configured to hold one of the plurality of sample containers in a temperature-controlled environment;
 an optical detector configured to observe and inspect the sample stored in one said sample container, said optical detector comprising a stage; and
 a transportation mechanism including an arm configured to move the sample container between the plurality of isothermal racks and the stage of the optical detector,
 wherein at least one of the isothermal rack, the stage of the optical detector, and the transportation mechanism includes a sample container holder comprising a protrusion configured to hold the lid of the sample container in a state of being lifted from the plate of the sample container, wherein
 the protrusion includes a lift portion configured to hold the lid of the sample container and a column configured to support the lift portion, and
 in response to determining that the sample container is transferred to any one of the isothermal rack, a stage of the optical detector, and the transportation mechanism, the lift portion is located in a gap between the lid and the plate of the sample container.

2. The inspection device according to claim 1, wherein
 the lift portion includes an inclined surface having a predetermined inclination with respect to a pedestal of the isothermal rack, a bottom surface of the sample container holder, or a pedestal of the transportation mechanism, and
 in response to determining that the sample container is transferred to the pedestal of the isothermal rack, the sample container holder, or the pedestal of the transportation mechanism, the lid of the sample container is lifted along the inclined surface of the lift portion.

3. The inspection device according to claim 2, wherein
 the lid of the sample container is held by the sample container holder in a state where a lower end of a sidewall of the lid is lower than an upper surface of the plate.

4. The inspection device according to claim 1, wherein the sample container holder is constructed to be vertically movable.

5. The inspection device according to claim 1, wherein a heater, configured to heat the lid of the sample container from above while the lid is lifted from the plate, is provided in at least one of the optical detector and the transportation mechanism.

6. The inspection device according to claim 5, wherein
 the lift portion includes an inclined surface having a predetermined inclination with respect to a bottom surface of a sample container holding part of the stage or the pedestal of the transportation mechanism, and
 in response to determining that the sample container is transferred to the sample container holding part of the stage or the pedestal of the transportation mechanism, the lid of the sample container is lifted along the inclined surface of the lift portion.

7. The inspection device according to claim 6, wherein
 in response to determining that the sample container is placed on the bottom surface of the sample container holding part of the stage or the pedestal of the transportation mechanism in a state where the lid is closed, the sample container holder is fixed to the stage or the transportation mechanism by the column, so that the lift portion of the sample container holder is located in the gap between the lid and the plate.

8. The inspection device according to claim 7, wherein
 the lid of the sample container is held by the sample container holder in a state where a lower end of a side wall of the lid is lower than an upper surface of the plate.

9. The inspection device according to claim 5, wherein
 the sample container holder is capable of lifting the lid of the sample container in a state where a lower end of a side wall of the lid is higher than an upper surface of the plate.

10. The inspection device according to claim 9, wherein
 a door is provided in at least one of the optical detector and the transportation mechanism, and is configured to limit movement of air in a space around the sample container placed on a sample container holding part of the stage or a pedestal of the transportation mechanism.

11. The inspection device according to claim 5, wherein
 at least one of the sample container holding part of the stage and the pedestal of the transportation mechanism is provided with a temperature detector configured to monitor a temperature of the sample stored in the sample container.

12. The inspection device according to claim 11, wherein
 heating with the heater is stopped in response to determining that the temperature of the sample monitored by the temperature detector is higher than a predetermined temperature.

13. The inspection device according to claim 11, wherein
 a temperature of the heater is set higher than a temperature set in the isothermal rack.

14. The inspection device according to claim 5, wherein
 the heater is sheet-shaped heater with a transparent portion at least in part, and includes a dew condensation detector configured to measure dew condensation on the lid of the sample container through the transparent portion of the heater.

\* \* \* \* \*